(12) United States Patent
Taniguchi

(10) Patent No.: US 6,733,865 B2
(45) Date of Patent: May 11, 2004

(54) COMPOSITE SHEET

(75) Inventor: Hiroaki Taniguchi, Kagawa-ken (JP)

(73) Assignee: Uni-Charm Corporation, Kawanoe (JP)

(*) Notice: Subject to any disclaimer, the term of this patent is extended or adjusted under 35 U.S.C. 154(b) by 92 days.

(21) Appl. No.: 09/951,550

(22) Filed: Sep. 14, 2001

(65) Prior Publication Data

US 2002/0054979 A1 May 9, 2002

(30) Foreign Application Priority Data

Sep. 19, 2000 (JP) .................................. 2000-283223

(51) Int. Cl.[7] .................................................. B32B 3/00
(52) U.S. Cl. ........................ 428/172; 428/198; 442/395; 442/394; 442/398
(58) Field of Search ...................... 428/172, 198; 442/395, 394, 398

(56) References Cited

U.S. PATENT DOCUMENTS 3,575,764 A * 4/1971 McFarren ................. 156/306.6

FOREIGN PATENT DOCUMENTS

| JP | 08126663 A | * 5/1996 | ........... A61F/13/15 |
| JP | 11-349702 | 12/1999 | |

* cited by examiner

*Primary Examiner*—Elizabeth M. Cole
(74) *Attorney, Agent, or Firm*—Lowe Hauptman Gilman & Berner LLP

(57) ABSTRACT

A composite sheet has a high total light transmittance over its entire region, the composite sheet including nonwoven fabric formed from thermoplastic synthetic resin fibers and a moisture permeable plastic film formed from an ester-based thermoplastic elastomer resin and joined by fusion to one surface of the nonwoven fabric. The composite sheet thus constituted has a total light transmittance of not less than 60% and not greater than 95%.

17 Claims, 7 Drawing Sheets

COMPOSITE SHEET

BACKGROUND OF THE INVENTION

This invention relates to a composite sheet comprising a nonwoven fabric formed from thermoplastic synthetic resin fibers and a plastic film formed from a thermoplastic synthetic resin and joined to one surface of the nonwoven fabric.

Japanese Patent Application Publication No. 1999-349702A discloses a porous sheet comprising a plastic sheet having a number of micro pores and partly embossed such that opaque regions having a total light transmittance of below 50% and transparent regions having a total light transmittance of 50% or above are formed in the sheet. In this porous sheet, the embossed portions define the transparent regions. The transparent regions account for 5–30% of a total area of the sheet. The sheet has a moisture permeability in the range of 0.8–4 g/100 cm$^2$·h. This porous sheet, when used as a back sheet of a disposable wearable article such as a disposable diaper or sanitary napkin, is effective to reduce humidity and heat buildup within the wearable article and permits us to see the excrements, e.g., urine and feces, absorbed in the wearable article though the transparent regions from outside of the article.

However, in the porous sheet as disclosed in the above-identified reference, the total light transmittance of the opaque regions, exclusive of the embossed portions, is below 50% and is insufficient for us to see the excrements through the opaque regions. The porous sheet only allows us to see a part of the excrements through the transparent regions. The reference also discloses a composite sheet having a nonwoven fabric laminated to the above porous sheet. However, the presence of the nonwoven fabric reduces a total light transmittance of the composite sheet and accordingly even at the transparent regions of the porous sheet.

SUMMARY OF THE INVENTION

It is an object of this invention to provide a composite sheet which shows high total light transmittance and moisture permeability and which, when used as a back sheet of a disposable wearable article, allows us to see the excrements absorbed in the article through the sheet, without difficulty, from outside of the article.

According to the present invention, there is provided a composite sheet comprises a nonwoven fabric formed from a thermoplastic synthetic resin fibers and a plastic film formed from a thermoplastic synthetic resin and joined to one surface of the nonwoven fabric.

The composite sheet further comprises the film being a moisture permeable film formed from any of urethane-based, ester-based and amide-based thermoplastic elastomer resins, the film and nonwoven fabric each having a total light transmittance of not less than 70% and not greater than 95% when measured according to a Japanese Industrial Standards (hereinafter referred to as JIS) K 7105A method, the film being joined by fusion to synthetic resin fibers constituting the nonwoven fabric, and the composite sheet having a total light transmittance of not less than 60% and not greater than 95% when measured according to a JIS K 7105A method.

This invention encompasses the following embodiments.

(1) The aforementioned film has a number of protuberances arranged in an intermittent manner and protruding toward the nonwoven fabric and flat portions extending in a substantially planar manner between adjacent protuberances, with the protuberances being joined by fusion to synthetic resin fibers constituting the nonwoven fabric.

(2) The composite sheet has a moisture permeability of not less than 1,000 g/m$^2$·24 Hr, when measured according to a JIS L 1099A-2 method.

(3) The composite sheet has a hydraulic pressure resistance of not less than 49 hpa, when measured according to a JIS L 1092A method.

(4) In a disposable wearable article which includes a liquid absorbent core interposed between a liquid permeable top sheet and a liquid impermeable back sheets, the composite sheet is used for the back sheet.

DETAILED DESCRIPTION OF THE PREFERRED EMBODIMENTS

The composite sheet in accordance with this invention is below described in detail with reference to the attached drawings.

Figure 1:
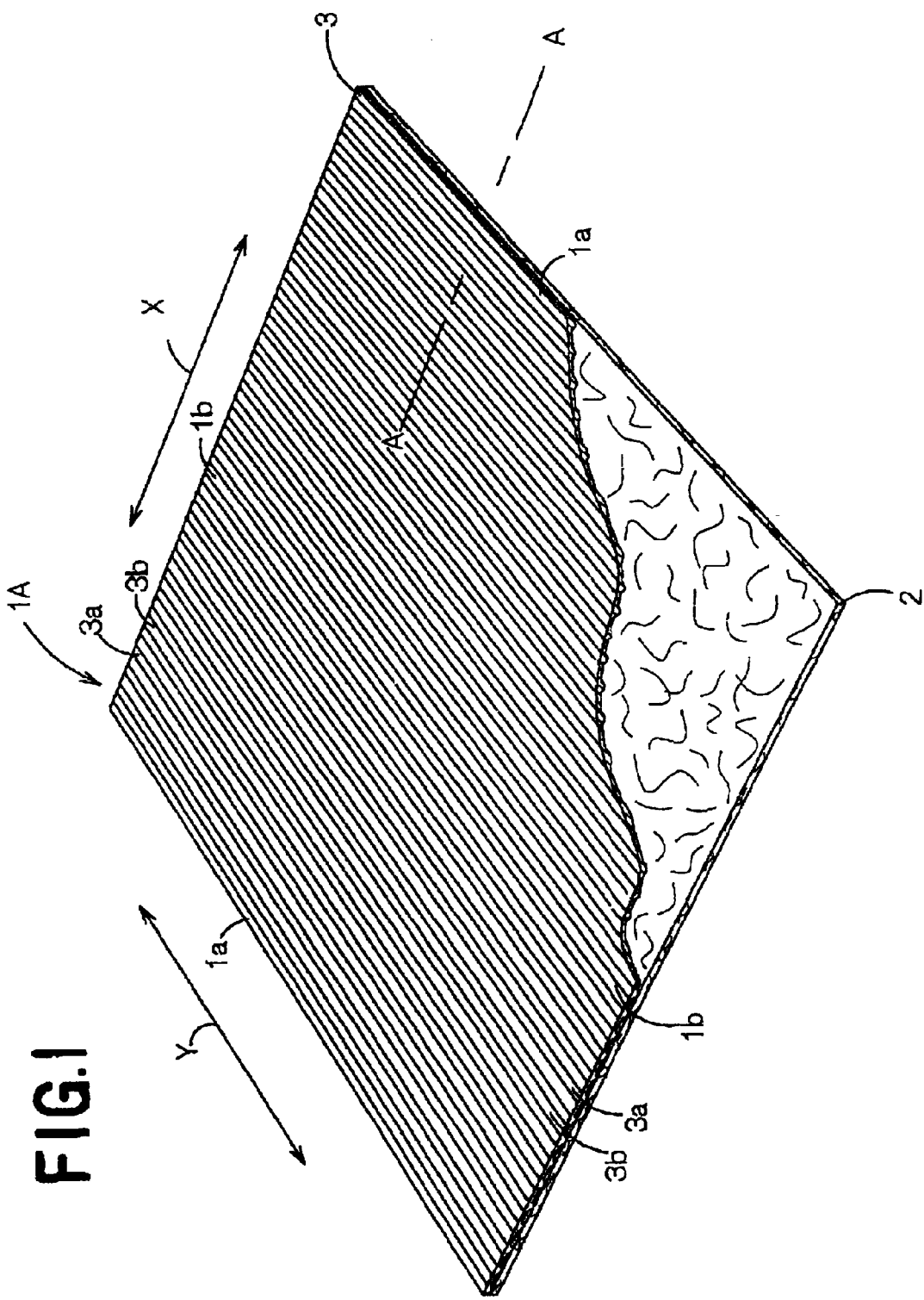
FIG. 1 is a partially cut-away perspective view of a composite sheet.
Figure 2:
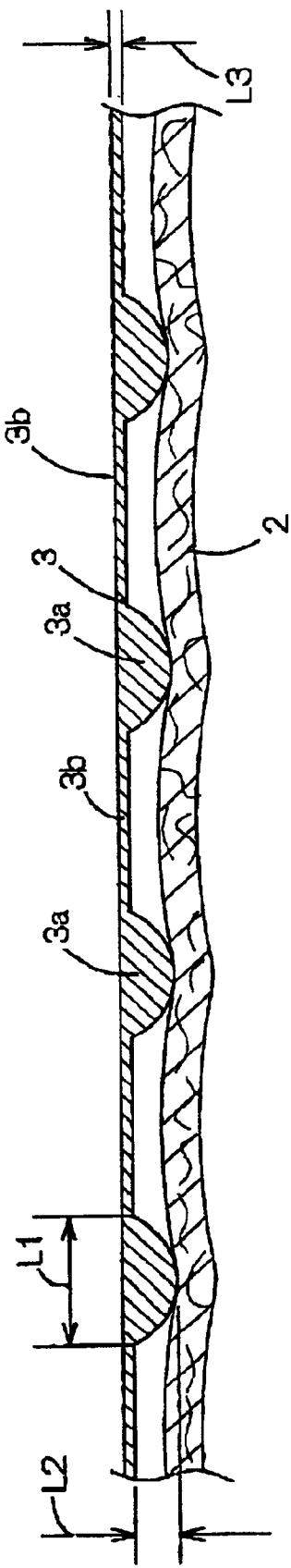
FIG. 2 is an end view taken along the line A—A of FIG. 1.
Figure 3:
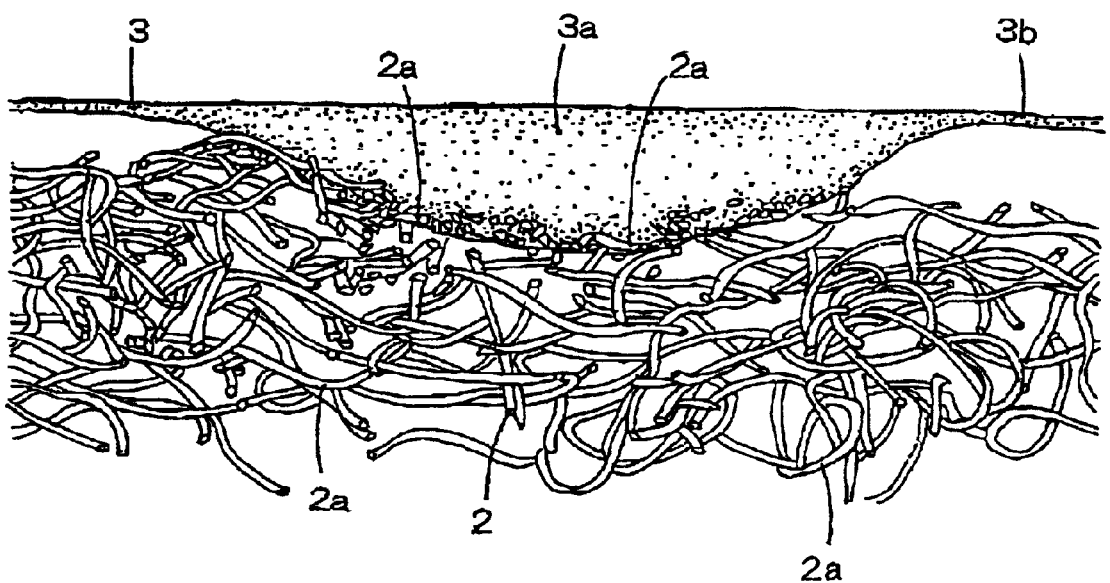
FIG. 3 is a view showing the end view of FIG. 2 in an enlarged fashion.

FIGS. 1 is a partially cut-away perspective view of a composite sheet 1A. FIG. 2 is an end view taken along the line A—A of FIG. 1. FIG. 3 is a view which shows the end view of FIG. 2 in an enlarged manner. In FIG. 1 and below-described FIGS. 4 and 6, a lateral direction is indicated by the arrow X and a longitudinal direction is indicated by the arrow Y.

The composite sheet 1A includes a nonwoven fabric 2 formed from thermoplastic synthetic resin fibers 2a and a plastic film 3 formed from a thermoplastic synthetic resin. The composite sheet 1A is constructed in two layers by such a way as to locate the nonwoven fabric 2 adjacent a bottom face of the film 3, and has opposite side edges 1a extending longitudinally in a parallel manner to each other and opposite end edges 1b extending laterally in a parallel manner to each other.

Examples of useful nonwoven fabrics 2 include those made by spun-lace and needle-punch techniques whereby constituent synthetic resin fibers 2a are mechanically entangled with each other, and those made by melt-blow, spun-bond, air-through, thermal-bond and chemical-bond techniques whereby synthetic resin fibers 2a are bonded to each other, either thermally or chemically.

Examples of useful synthetic resin fibers 2a include polyolefinic fibers such as polypropylene and polyethylene, polyester fibers such as polyethylene terephthalate and polybutylene terephthalate, polyamide fibers such as nylon 66 and nylon 6, acrylic fibers, polyethylene/polypropylene or polyester sheath-core and side-by-side conjugate fibers.

The film 3 is formed from an ester-based thermoplastic elastomer resin, and permeable to moisture. The elastomer resin is a block copolymer consisting of hard and soft segments. The hard segments comprise polyester derived either from aromatic dicarboxylic acid and aliphatic diol or from aliphatic dicarboxylic acid and aromatic diol. The soft segments comprise polyether.

The following explains a mechanism of moisture vapor transmission through the film 3. The film 3 consists of hard segments as molecule-constraining constituents that serve to prevent plastic deformation, and soft segments as flexible constituents that permit transmission of moisture vapor. The hard and soft segments are located in a random manner in the film 3. In the hard segments, polymeric chains of polyester form a crystalline phase. In the soft segments, polymeric chains of polyether form a non-crystalline phase. In the soft segments which are, in their ordinary state, placed under a temperature of not lower than its glass transition temperature, neighboring polymeric chains of polyether are dislocated from each other as a result of micro-Brownian motion to form a void between them, which is larger in size than a molecule (particle diameter of about 3.5 Å) of moisture vapor. By the force between molecules of polyester and polyether, molecules of moisture vapor are allowed to adsorb on a top side of the film 3 and then pass through the voids present in the soft segments into an interior of the film 3. If a vapor pressure is lower at a back side than at a top side of the film 3, the molecules of moisture vapor are allowed to move through the voids toward the back side of the film 3, pass through the film 3 and exit from the back side of the film 3 to outside.

The film 3 may be made from either one of urethane-based and amide-based thermoplastic elastomer resins, instead of an ester-based thermoplastic elastomer resin.

The film 3 includes protuberances 3a arranged in plural spaced-apart parallel lines and extending in one direction on its surface facing the nonwoven fabric 2, and flat portions 3b extending in a substantially planar manner between adjacent protuberances 3a. In the film 3, the protuberances 3a are spaced apart at regular intervals and extend longitudinally in a parallel manner to each other and the flat portions 3b extend longitudinally between adjacent protuberances 3a in a parallel manner to each other.

The aforementioned nonwoven fabric 2 and film 3 both have a total light transmittance of not less than 70% and not greater than 95%. The composite sheet 1A has a total light transmittance of not less than 60% and not greater than 95%. These values for total light transmittance are determined according to JIS K 7105.

In the composite sheet 1A, the nonwoven fabric 2 and film 3 are united together by joining by fusion the protuberances 3a of the film 3 to the synthetic resin fibers 2a constituting the nonwoven fabric 2 while in the state of retaining their fibrous form, as shown in FIG. 3.

The composite sheet 1A has a moisture permeability of not less than 1,000 g/m²·24 Hr and a hydraulic pressure resistance of not less than 49 hpa. These values for moisture permeability and hydraulic pressure resistance are determined according to a JIS L 1099A-2 method and a JIS L 1092A method, respectively. The composite sheet 1A shows excellent moisture permeability and liquid impermeability.

In the composite sheet 1A, a peel strength between the nonwoven fabric 2 and film 3 is preferably not less than 400 mN/25 mm. If the peel strength is below 400 mN/25 mm, there is an increasing tendency for the nonwoven fabric 2 and film 3 to be separated from each other, possibly resulting in the failure to retain an integral form of the composite sheet 1A.

Preferably, the nonwoven fabric 2 has a basis weight in the range of 10–50 g/m². If the basis weight is below 10 g/m², the nonwoven fabric 2 decreases in strength to the extent that the composite sheet 1A may undergo breakage at the nonwoven fabric 2. If the basis weight exceeds 50 g/m², it may become difficult to maintain a total light transmittance of the nonwoven fabric at a value of not less than 70% and not greater than 95%.

Preferably, the protuberance 3a of the film 3 has a width dimension L1 in the range of 0.2–2.0 mm and a maximum thickness dimension L2 in the range of 15–100 μm. If the width dimension L1 is below 0.2 mm and the maximum thickness dimension L2 is below 15 μm, the film 3 may be little joined by fusion to synthetic resin fibers 2a constituting the nonwoven fabric 2 to reduce a peel strength between the nonwoven fabric 2 and film 3, thereby making it difficult to maintain the peel strength between them at a value of not less than 400 mN/25 mm. If the width dimension L1 exceeds 2.0 mm and the maximum thickness dimension L2 exceeds 100 μm, a proportion of the film 3 that is occupied by the protuberances 3a increases to such an extent as to increase rigidity of the film 3 and reduce flexibility of the composite sheet 1A.

Preferably, the flat portion 3b of the film 3 has a thickness dimension L3 in the range of 5–90 μm. If the thickness dimension L3 is below 5 μm, the film strength at the flat portions 3b may decrease to possibly result in the breakage of the composite sheet 1A at the film 3. If the thickness dimension L3 exceeds 90 μm, the moisture permeability of the film at the flat portions 3b may decrease to result in the difficulty to maintain the moisture permeability of the composite sheet at a value of not less than 1,000 g/m²·24 Hr.

Figure 4:
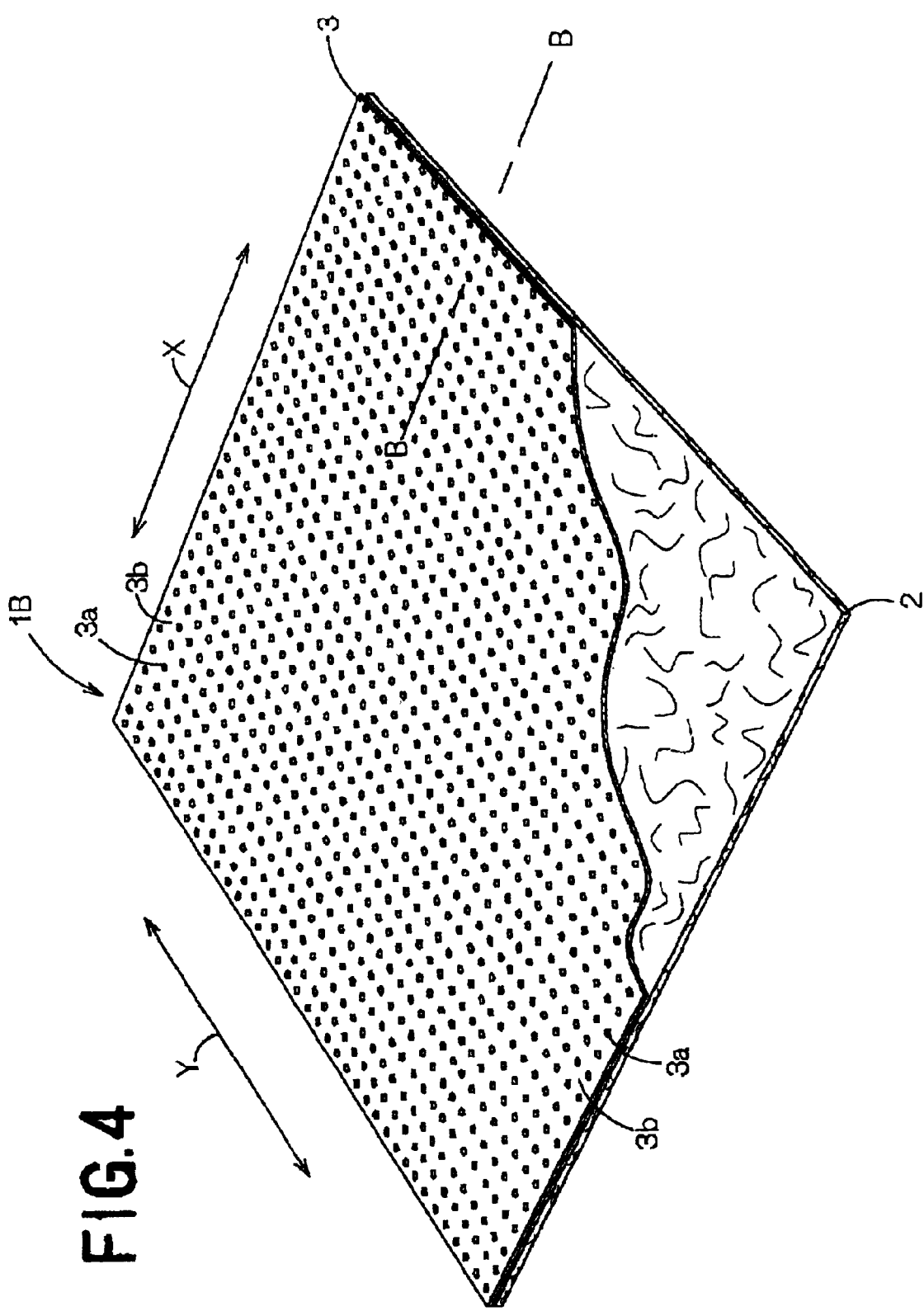
FIG. 4 is a partially cut-away perspective view of a composite sheet embodiment which differs from the embodiment shown in FIG. 1.
Figure 5:
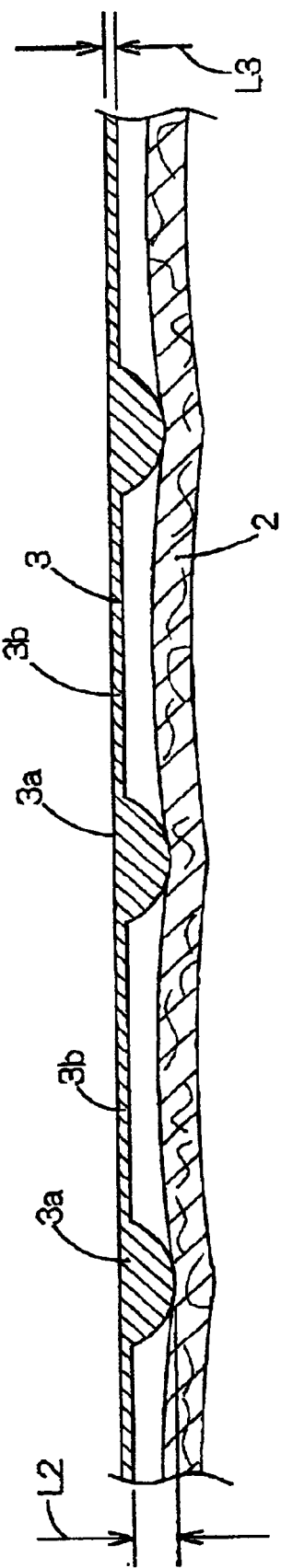
FIG. 5 is an end view taken along the line B—B of FIG. 4.

FIG. 4 is a partially cut-away perspective view, illustrating a composite sheet 1B in an embodiment different from that shown in FIG. 1. FIG. 5 is an end view taken along the line B—B of FIG. 4. The composite sheet 1B shown in FIG. 4 includes a nonwoven fabric 2 formed from thermoplastic synthetic fibers 2a and a plastic film 3 formed from a thermoplastic synthetic resin. The composite sheet 1B of this embodiment differs from the composite sheet shown in FIG. 1 by the way which follows.

The film 3 has a number of protuberances 3a distributed in a dotted fashion throughout its surface facing the nonwoven fabric and flat portions 3b which extend in a substantially planar manner between adjacent protuberances 3a. In the composite sheet 1B, the nonwoven fabric 2 and film 3 are united together by joining by fusion the protuberances 3a of the film 3 to the synthetic resin fibers 2a constituting the nonwoven fabric 2 while in the state of retaining their fibrous form.

The respective total light transmittances of the nonwoven fabric 2, film 3 and composite sheet 1B, moisture permeability and hydraulic pressure resistance of the composite sheet 1B, basis weight of the nonwoven fabric 2, composition of the film 3, maximum thickness dimension L2 of the protuberance 3a and thickness dimension L3 of the flat portion 3b are all similar in values to those specified for the embodiment shown in FIG. 1.

Preferably, the protuberance 3a of the film 3 has an area in the range of 0.001–0.200 cm² and the protuberances 3a account for 5–70% of a total area of the composite sheet 1B.

If the area of protuberance 3a is below 0.001 cm² and the proportion in area of the composite sheet that is occupied by the protuberances 3a is below 5%, a peel strength between the nonwoven fabric 2 and film 3 decreases to result in the difficulty to maintain the peel strength between them at a value of not less than 400 mN/25 mm. If the area of protuberance 3a exceeds 0.200 cm² and the proportion in area of the composite sheet that is occupied by the protuberances 3a exceeds 70%, a proportion of the film 3 that is occupied by the protuberances 3a increases to such an extent as to reduce flexibility of the composite sheet 1B.

Besides the above-shown composite sheet embodiments 1A and 1B, the composite sheet may be constructed such that the synthetic resin fibers 2a constituting the nonwoven fabric 2 are joined by fusion to an entire surface of the film 3. Also, in the case where the nonwoven fabric 2 is formed from polyolefinic fibers, the nonwoven fabric 2 may preferably be treated with a primer to facilitate joining of the nonwoven fabric 2 to the film 3.

Figure 6:
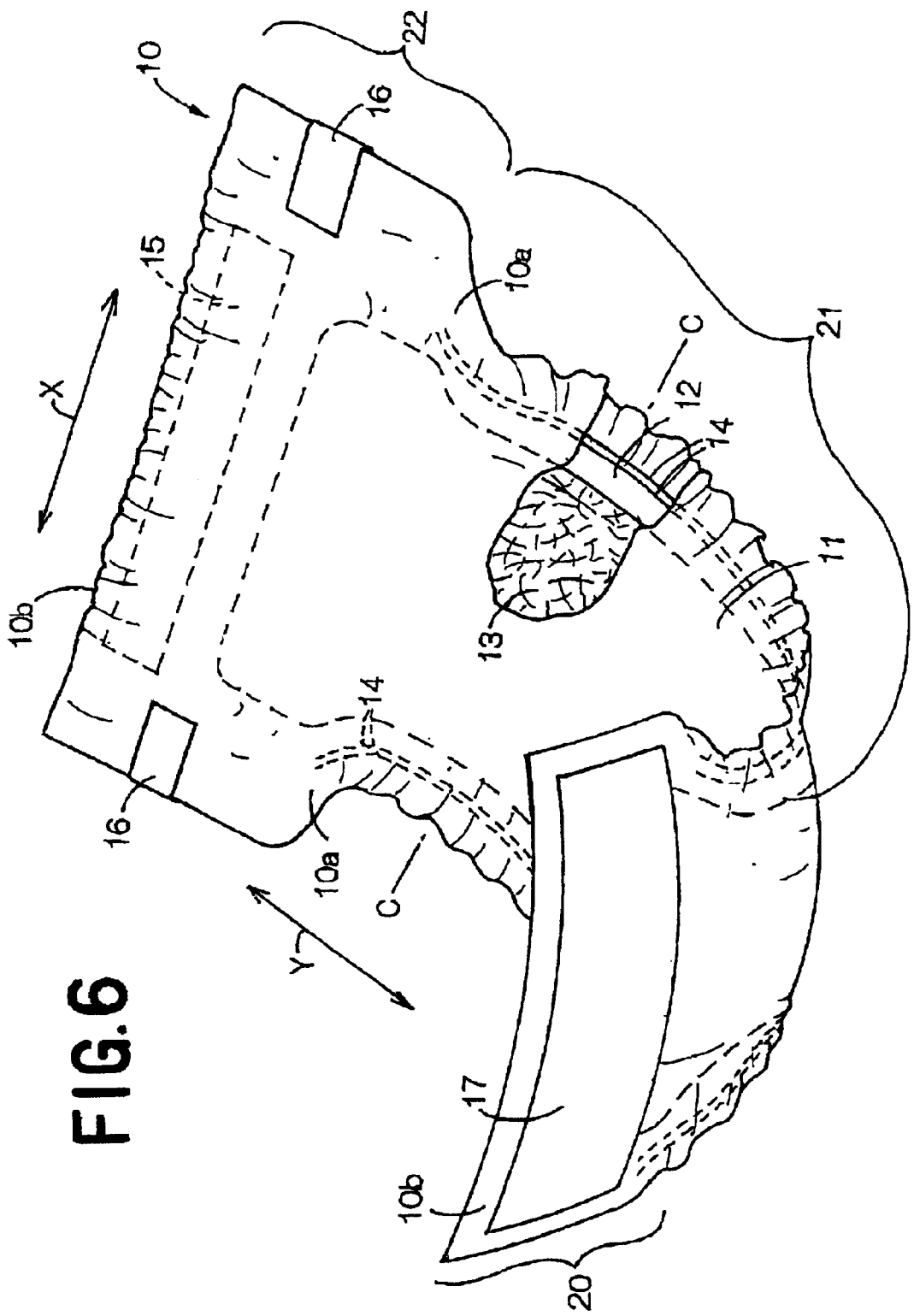
FIG. 6 is a partially cut-away perspective view of a disposable diaper using the composite sheet of FIG. 1 for its back sheet.
Figure 7:
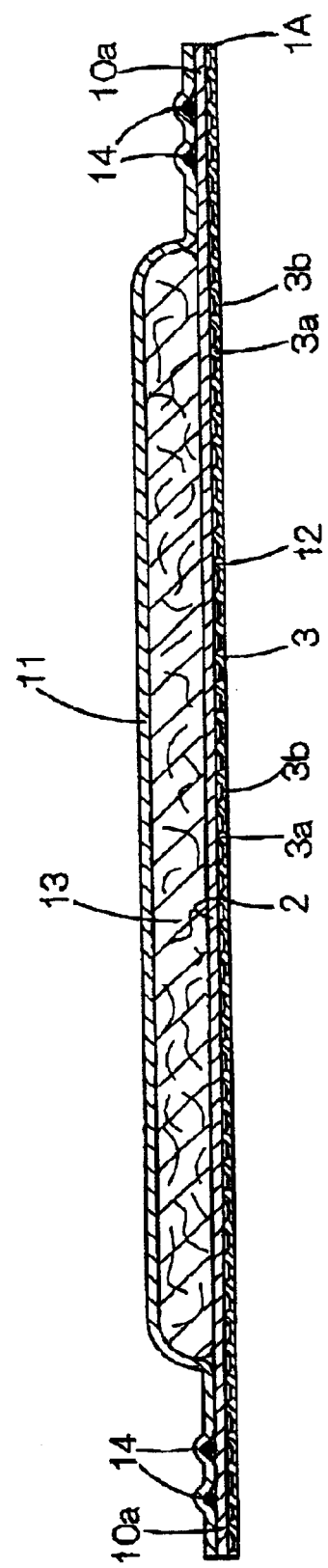
FIG. 7 is an end view taken along the line C—C of FIG. 6.

FIG. 6 is a partially cut-away perspective view of a disposable diaper incorporating the composite sheet 1A of FIG. 1 as a back sheet 12. FIG. 7 is an end view taken along the line C—C of FIG. 6. The diaper 10 has a liquid pervious top sheet 11, a liquid impervious back sheet 12, and a liquid absorbent core 13 interposed between the top sheet 11 and back sheet 12 and completely enveloped by and joined to a tissue paper (not shown). The core 13 is joined, via the tissue paper, to the top sheet 11 and the back sheet 12.

The diaper has a front waist region 20, a rear waist region 22 and a crotch region 21 positioned between the front and rear waist regions 20 and 22, along its longitudinal direction. The diaper also has longitudinally-extending side edges 10a and laterally-extending end edges 10b. The side edges 10a are both curved laterally inwardly of the diaper 10 at the crotch region 21.

The diaper 10 uses the composite sheet 1A shown in FIG. 1 for the back sheet 12. The back sheet 12 is oriented such that the nonwoven fabric 2 faces toward an inside of the diaper 10 and the film 3 defines an outer face of the diaper 10.

A set of leg-encircling elastic members 14 are attached to each side edge 10a in a stretched state for longitudinal stretch and contraction. A waist-encircling band-like elastic member 15 is attached to the end edge 10b in the rear waist region 22 for lateral stretch and contraction. Those elastic members 14 and 15 are interposed between the top sheet 11 and the back sheet 12 and secured to these sheets 11 and 12.

In the rear waist region 22, a tape fastener 16 is provided to extend laterally inwardly from each side edge 10a of the diaper 10. A target tape 17 is attached to a back face of the back sheet 12 in the front waist region 20 to provide a zone for securing the tape fastener 16 thereto. When the diaper 10 is applied to a wearer, the front and rear waist regions 20 and 22 are connected to each other by securing the tape fastener 16 onto the target tape 17.

A nonwoven fabric, apertured plastic film or other liquid pervious sheet, preferably a liquid pervious and hydrophilic sheet, can be used to form the top sheet 11. The core 13 comprises a mixture containing fluff pulps, high-absorbent polymer particles and thermoplastic synthetic resin fibers and is compressed to a thickness as desired. Examples of useful high-absorbent polymers include starch-based, cellulose-based and synthetic polymers.

A hot-melt adhesive or heat seal, sonic seal or other thermal welding means can be utilized to secure the top and back sheets 11, 12 to each other, join the core 13 and secure the elastic members 14, 15, tape fastener 16 and target tape 17 to the top and back sheets 11, 12.

Since the back sheet 11 comprises the composite sheet 1A having a high total light transmittance, the diaper 10 permits us to see the excrements absorbed in the diaper 10 through an entire region of the bask sheet 11. In addition, the back sheet 11, because of it high moisture permeability and hydraulic pressure resistance, reduces heat and moisture buildup within the diaper 10 and prevents the excrements from passing through the back sheet 11.

Other than a disposable diaper 10, the composite sheet can also be used for a back sheet of a sanitary napkin.

The following Example 1 and Comparative Example 1 illustrate the composite sheet in accordance with the present invention and a porous sheet for comparison to Example 1, respectively.

A composite sheet of Example 1 is constructed from a plastic film formed of an ester-based thermoplastic elastomer resin (product name: PELPREBNE GP-550, manufactured by Toyobo Co., Ltd.) and a spun-bonded nonwoven fabric (product name: ECOURE, manufactured by Toyobo Co., Ltd.). In Example 1, the above-specified elastomer resin is kneaded and melted in an extruder and then extruded from a T-die (resin temperature: 230° C., extrusion rate: 60 m/min) onto the nonwoven fabric for joint thereof. The nonwoven fabric is formed from a number of ester-based fibers. The film has protuberances arranged in spaced-apart parallel lines and extending in one direction. These protuberances are joined by fusion to the synthetic resin fibers constituting the nonwoven fabric.

A composite sheet of Comparative Example 1 is constructed from an olefin-based plastic film having a number of micro pores and a spun-bonded nonwoven fabric (product name: ECOURE, manufactured by Toyobo Co., Ltd.). The film is loaded with calcium carbonate. Stretching of the film results in the formation of those micro-pores therein. The nonwoven fabric is formed from a number of ester-based fibers. In Comparative Example 1, the film is joined to the nonwoven fabric in an intermittent manner by adhesives.

The composite sheets of Example 1 and Comparative Example 1 were measured for total light transmittance, moisture permeability and hydraulic pressure resistance. The results are shown in Table 1. The total light transmittance, moisture permeability and hydraulic pressure resistance were measured according to a JIS K 7105A method, JIS L 1099A-2 method and JIS L 1092A method, respectively.

TABLE 1

|  | Example 1 | Comparative Example 1 |
| --- | --- | --- |
| Basis weight of the nonwoven fabric (g/m²) | 15 | 15 |
| Thickness dimension of film protuberance (µm) | 20 | 22 |
| Thickness dimension of composite sheet (µm) | 100 | 100 |
| Properties |  |  |
| Total light transmittance (%) | 84.3 | 63.5 |
| Moisture permeability (g/m² · 24 Hr) | 3296 | 1930 |
| Hydraulic pressure resistance (hpa) | over 1000 | over 1000 |

As indicated in Table 1, the composite sheet of Example 1 shows the increased total light transmittance, moisture permeability and hydraulic pressure resistance, compared to the composite sheet of Comparative Example 1.

The composite sheet in accordance with the present invention comprises a film and a sheet member united together by joining, by fusion, a plastic film formed of any of urethane-based, ester-based and amide-based thermoplastic elastomer resins to thermoplastic synthetic resin fibers constituting a nonwoven fabric, and accordingly shows a high level of total light transmittance of not less than 60% and not greater than 95% over its entire region and also has high moisture permeability and hydraulic pressure resistance.

A disposable wearable article using the composite sheet for its back sheet permits us to see the excrements absorbed in the article through an entire region of the back sheet. Also, the increased moisture permeability and hydraulic pressure resistance of the back sheet not only reduces humidity and heat buildup within the diaper, but also prevents the excrements from passing through the back sheet.

What is claimed is:

1. A composite sheet, comprising a nonwoven fabric formed from thermoplastic synthetic resin fibers and a moisture permeable plastic film formed from a thermoplastic synthetic resin and joined to one surface of the nonwoven fabric, wherein:

said thermoplastic synthetic resin of said plastic film is any of urethane-based, ester-based and amide-based thermoplastic elastomer resins, and is a block copolymer having hard segments as molecule-constraining constituents that serve to prevent plastic deformation and soft seaments as flexible constituents that permit transmission of moisture vapor.

said nonwoven fabric and film both have a total light transmittance of not less than 70% and not greater than 95% when measured according to a JIS K 7105A method;

said film is joined by fusion to the synthetic resin fibers constituting said nonwoven fabric, and said composite sheet has a total light transmittance of not less than 60% and not greater than 95% when measured according to a JIS K 7105A method.

2. The composite sheet of claim 1 wherein said film includes a number of protuberances arranged in an intermittent manner and protruding toward said nonwoven fabric and flat portions extending in a substantially planar manner between adjacent protuberances, and wherein said protuberances are joined by fusion to the synthetic resin fibers constituting the nonwoven fabric.

3. The composite sheet of claim 1 wherein said composite sheet has a moisture permeability of not less than 1,000 g/m²·24 Hr, when measured according to a JIS L 1099A-2 method.

4. The composite sheet of claim 1 wherein said composite sheet has a hydraulic pressure resistance of not less than 49 hpa, when measured according to a JIS L 1092A method.

5. A disposable wearable article, comprising a liquid absorbent core interposed between a liquid pervious top sheet and a liquid impervious back sheet which is a composite sheet;

said composite sheet comprising a nonwoven fabric formed from thermoplastic synthetic resin fibers and a moisture permeable plastic film formed from a thermoplastic synthetic resin and joined to one surface of the nonwoven fabric, wherein:

said thermoplastic synthetic resin of said plastic film is any of urethane-based. ester-based and amide-based thermoplastic elastomer resins, and is a block copolymer having hard segments as molecule-constraining constituents that serve to prevent plastic deformation and soft segments as flexible constituents that permit transmission of moisture vapor;

said nonwoven fabric and film both have a total light transmittance of not less than 70%a and not greater than 95% when measured according to a JIS K 7105A method:

said film is joined by fusion to the synthetic resin fibers constituting said nonwoven fabric; and said composite sheet has a total light transmittance of not less than 60% and not treater than 95% when measured according to a JIS K 7105A method.

6. The article of claim 5, wherein an entirety of said plastic film has a total light transmittance of not less than 70% and not greater than 95% when measured according to a JIS K 7105A method.

7. The article of claim 5, wherein said plastic film includes a number of intermittently arranged protuberances protruding toward said nonwoven fabric; and generally flat portions positioned between adjacent said protuberances, wherein said protuberances are joined by fusion to the synthetic resin fibers of the nonwoven fabric.

8. The article of claim 6, wherein said plastic film includes a number of intermittently arranged protuberances protruding toward said nonwoven fabric; and generally flat portions positioned between adjacent said protuberances, wherein said protuberances are joined by fusion to the synthetic resin fibers of the nonwoven fabric.

9. The article of claim 6, wherein a thickness of said protuberances as measured in a direction normal to said plastic film is from 15 to 100 µm.

10. A composite sheet, comprising a nonwoven fabric formed from thermoplastic synthetic resin fibers and a moisture permeable plastic film formed from a thermoplastic synthetic resin and joined to one surface of the nonwoven fabric, wherein:

said thermoplastic synthetic resin of said plastic film is any of urethane-based, ester-based and amide-based thermoplastic elastomer resins;

an entirety of said plastic film has a total light transmittance of not less than 70% and not greater than 95% when measured according to a JIS K 7105A method; and said plastic film is joined by fusion to the synthetic resin fibers constituting said nonwoven fabric.

11. The composite sheet of claim 10, wherein said nonwoven fabric has a total light transmittance of not less than 70% and not greater than 95% when measured according to a JIS K 7105A method; and said composite sheet has a total light transmittance of not less than 60% and not greater than 95% when measured according to a JIS K 7105A method.

12. The composite sheet of claim 10, wherein said plastic film includes a number of intermittently arranged protuberances protruding toward said nonwoven fabric; and flat portions positioned between adjacent said protuberances, wherein said protuberances are joined by fusion to the synthetic resin fibers constituting the nonwoven fabric.

13. The composite sheet of claim 10, wherein said composite sheet has a moisture permeability of not less than 1,000 g/m²·24 Hr, when measured according to a JIS L 1099A-2 method.

14. The composite sheet of claim 10, wherein said composite sheet has a hydraulic pressure resistance of not less than 49 hpa, when measured according to a JIS L 1092A method.

15. The composite sheet of claim 10, wherein a greatest material thickness of said plastic film in a region of said protuberances is from 15 to 100 μm.

16. The composite sheet of claim 10, wherein said thermoplastic synthetic resin of said plastic film is a block copolymer having hard segments as molecule-constraining constituents that serve to prevent plastic deformation and soft segments as flexible constituents that permit transmission of moisture vapor.

17. The composite sheet of claim 11, wherein a greatest material thickness of said plastic film in a region of said protuberances is from 15 to 100 μm.

\* \* \* \* \*